Figure 1:
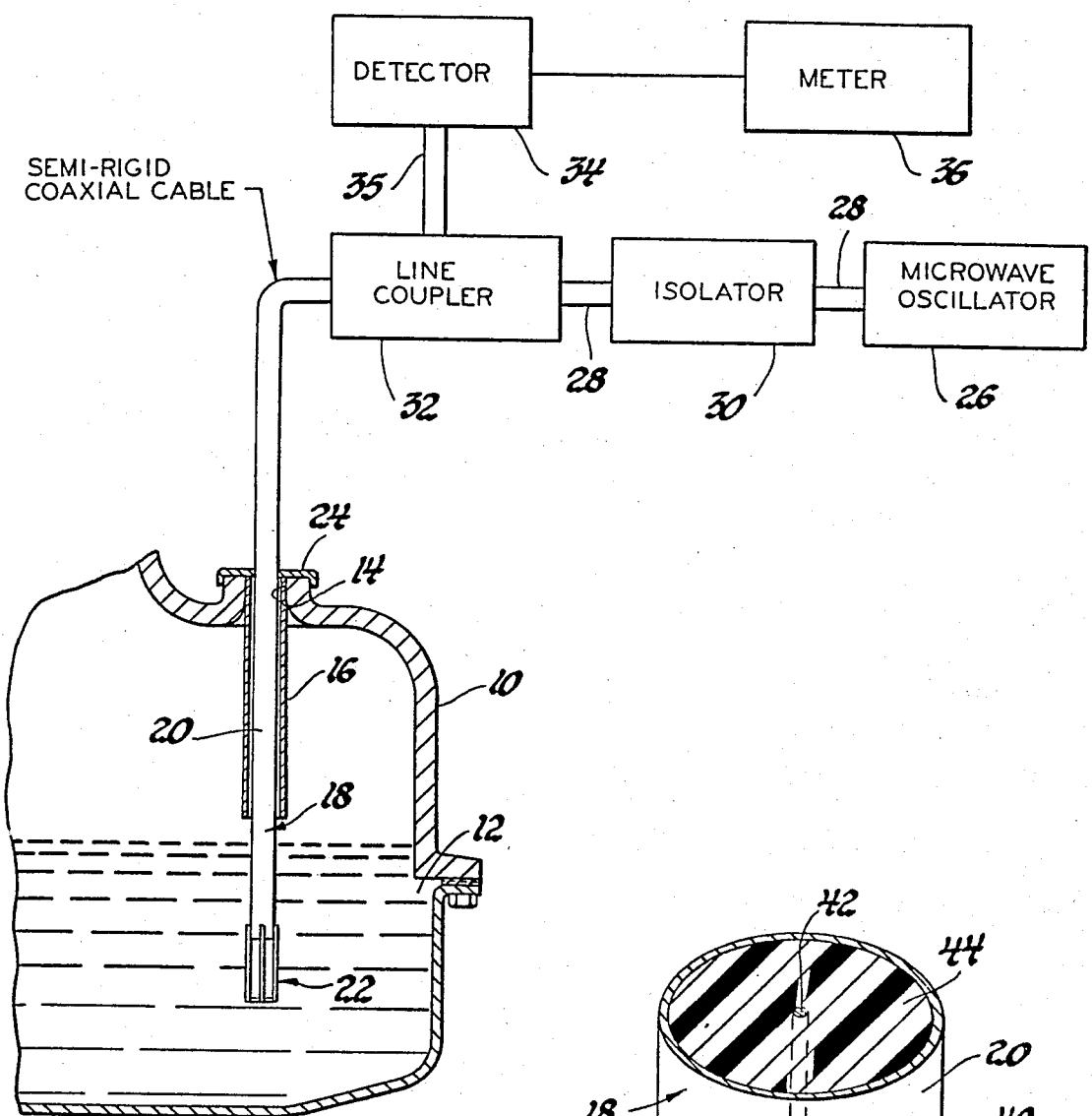

United States Patent [19]

Nagy et al.

[11] Patent Number: 4,543,823
[45] Date of Patent: Oct. 1, 1985

[54] MICROWAVE PROBE FOR DETECTING OIL LEVEL

[75] Inventors: Louis L. Nagy, Warren; Michael J. O'Rourke, Sterling Heights, both of Mich.

[73] Assignee: General Motors Corporation, Detroit, Mich.

[21] Appl. No.: 671,600

[22] Filed: Nov. 15, 1984

Related U.S. Application Data

[62] Division of Ser. No. 372,470, Apr. 28, 1982, Pat. No. 4,503,384.

[51] Int. Cl.[4] ............................................. G01R 27/04
[52] U.S. Cl. .................................. 73/304 C; 324/61 P; 324/58.5 R
[58] Field of Search .................... 73/61 R, 304 C; 324/437, 361, 58.5 R, 58.5 A, 58.5 B, 61 P

[56] References Cited

U.S. PATENT DOCUMENTS

| | | |
|---|---|---|
| 3,226,615 | 12/1965 | Nagel ................................ 324/61 P |
| 3,572,119 | 3/1971 | Bak . |
| 3,626,284 | 12/1971 | Bak . |
| 3,703,829 | 11/1972 | Dougherty ..................... 324/58.5 B |
| 3,812,422 | 5/1974 | De Carolis . |
| 4,345,202 | 8/1982 | Nagy .............................. 324/58.5 B |
| 4,503,384 | 3/1985 | Nagy ................................. 324/61 P |

Primary Examiner—Stanley T. Krawczewicz
Assistant Examiner—Jose M. Solis
Attorney, Agent, or Firm—Warren D. Hill

[57] ABSTRACT

A microwave probe for measuring the amount of soot or water in engine crankcase oil and/or detecting the level of oil comprises a coaxial cable having a tip including five substantially parallel wires shorted together at one end and connected at the other end to the coaxial cable, one of the wires being connected to the center wire of the coaxial cable and the other four wires being connected to the sheath of the coaxial cable. The size and geometry of the wires is selected so that the impedance of the tip when immersed in oil substantially matches the impedance of the coaxial cable.

3 Claims, 2 Drawing Figures

MICROWAVE PROBE FOR DETECTING OIL LEVEL

This is a division of application Ser. No. 372,470 filed on Apr. 28, 1982, now U.S. Pat. No. 4,503,384 issued 3/5/85.

This invention relates to a microwave probe for measurement of dielectric constants and, more particularly, to such a probe for the measurement of contaminants in engine crankcase oil and for the detection of oil level.

It has been found that microwave sensors responsive to the dielectric constants of a fluid are useful in a number of ways to inspect the condition of the crankcase oil of an internal combustion engine. For example, when an engine is newly built and first tested a gasket or casting leak can result in water entering the crankcase oil. Thus as an inspection method it is desirable to insert a probe into the crankcase through the dipstick access port to measure the dielectric constant of the oil for the detection of ½% of water in the oil. As another example, in the case of diesel engines, soot build-up in the oil should be detected to determine when to change the oil. A method of detecting soot in engine oil using microwaves is set out in the U.S. Pat. No. 4,345,202, issued Aug. 17, 1982, to Nagy et al, filed Dec. 19, 1980. Still another application of sensing the dielectric constant of the fluid in an engine crankcase is the measurement of the oil level wherein the presence of air or vapor in the probe along with oil provides a marked difference of dielectric constant from that of a probe fully immersed in oil. While there have been other microwave sensors for measuring the dielectric constant of liquids, in particular, or of fluids, there are some particular constraints which must be observed for the successful application of such measurements in an engine crankcase. One is that since oil in some circumstances is rather viscous there is a tendency for the oil to hang up on or in a measurement probe so that as oil is changed or the contamination of oil changes some of the old oil tends to remain in the probe to give rise to some error in the measurement of the current oil condition. Thus the probe must be constructed to allow very free oil flow-through and to minimize any pockets or other structure which would encourage hang up of oil in the probe. Also the probe must be rugged and yet small enough to be inserted through a dipstick access hole or passage tube for entry into the crankcase, and the probe should be insensitive to metal objects near the probe location. In addition, for maximum sensitivity, the characteristic impedance of the probe tip must be matched to that of the associated transmission line. Finally, where the probe is to be used as a permanent part of the vehicle equipment it should be simple and inexpensive to manufacture.

It is therefore a general object of this invention to provide a microwave probe which facilitates free flow of liquid therethrough and has an impedance which matches that of the associated transmission line.

A further object of the invention is to provide such a probe which is small, rugged and of inexpensive construction.

It is a further object of the invention to provide such a probe which is not affected by the presence of nearby metal objects.

The invention is carried out by a microwave probe having a coaxial cable with an outer sheath and a central conductor and a tip attached to the end of the cable including a center wire joined to or comprising an extension of the center conductor and a plurality, preferably four, outer wires connected to the sheath and connected at their distal ends to the center conductor by a short, the wire size and geometry being such that the impedance of the tip substantially matches the characteristic impedance of the coaxial cable.

Figure 2:
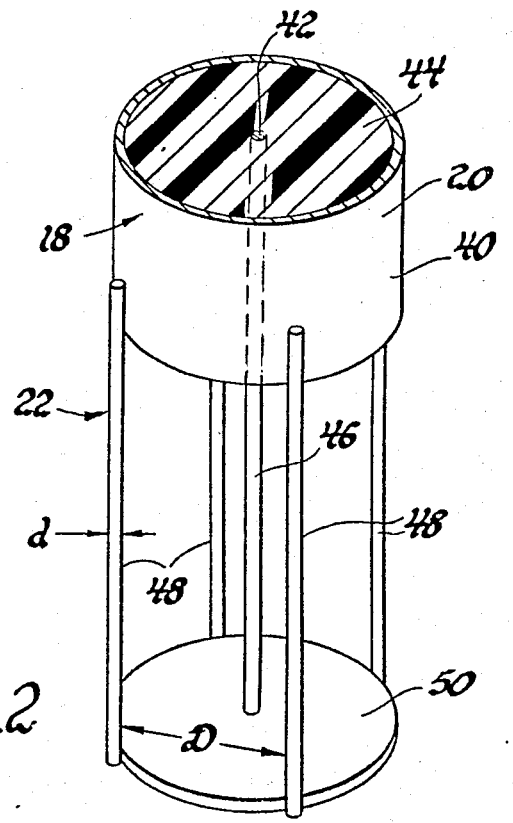

The above and other advantages will be made more apparent from the following specification taken in conjunction with the accompanying drawings wherein like reference numerals refer to like parts and wherein FIG. 1 is a block diagram of a microwave circuit coupled to a microwave probe in an engine crankcase, and FIG. 2 is an isometric view of a microwave probe according to the invention.

FIG. 1 shows a partly broken away cross-sectional view of an internal combustion engine housing 10 containing oil 12 in the crankcase and an opening 14 for a dipstick, the opening being optionally provided with a tube 16 fitting within the opening to provide a passage for a dipstick as is well-known in the prior art. A microwave probe 18 comprising a semi-rigid coaxial cable 20 and a cage-like tip 22 on its lower end extends into the passage formed by the opening 14 and tube 16 so that the tip 22 is positioned in the crankcase preferably just at the minimum desired level of the oil. A collar or stop 24 secured to the probe and positioned to seat against the housing at the outer surface of the opening 14 establishes the position of the tip 22. The tip position in the vertical sense is important where the probe is to be used as an oil level sensor. If, however the probe is only to have a contamination sensing function, then it may well be placed lower in the crankcase somewhat below the minimum liquid level. A microwave oscillator 26 is connected by means of waveguides 28 through an isolator 30 to the probe 18. A line coupler 32 inserted in the circuit comprises an antenna wire extending into the waveguide to sense the value of the standing wave at that point, the standing wave being a function of the microwave energy reflected from the probe. A diode detector 34 connected to the line coupler 32 by a coaxial cable 35 provides a measure of the microwave energy reflected from the probe 18 and a meter 36 connected thereto displays an indication of the condition of the oil 12 in terms of contaminant content and/or the liquid level.

The detailed structure of the probe is shown in FIG. 2. The coaxial cable, preferably a conventional 50 ohm cable, is illustrated as a cylindrical conductive sheath 40 and a central conductor 42 and the space between the two is filled with a dielectric material 44 all in accordance with conventional coaxial cable technology. The tip 22 comprises five substantially parallel wires including a center wire 46 and four outer wires 48. The center wire 46 may be a continuation of the center conductor 42 or it may be a separate wire welded to the conductor 42. The outer wires 48 are each joined as by welding to the outer sheath 40. A conductive shorting disc 50 is welded at its center to the center wire 46 and at its rim to the distal end of each outer wire 48. Thus the probe is a cage-like structure characterized by a plurality of widely-spaced wires shorted at one end in an open configuration to allow free oil flow through the tip without pockets to trap oil and also without screens or mesh walls which might clog with foreign particles or otherwise impede the free flow of oil through the tip. The shorting disc 50 could be replaced by another configuration of conductor such as a sphere.

It is important for the tip to have an impedance which substantially matches that of the coaxial cable 20 when the tip is immersed in oil. If the tip and cable have impedances within about 10% of each other, they are substantially matched. Matching the tips characteristic impedance to that of the coaxial cable increases the dependence of the resulting voltage standing wave within the cable on the dielectric medium within the tip to increase detection capability. If the match is perfect the sensitivity is maximized, but some tolerance is allowable in a practical system. In addition, when the tip is filled with oil and matched with the cable impedance the only significant discontinuity in the probe is at the short, whereas if the tip had a substantially different impedance from the cable the interface between the cable and the tip would provide a second discontinuity. Two discontinuities would result in a composite reflecting signal making the detection and analysis of the signal difficult whereas the matched impedance tip offers no such difficulty. From transmission line theory it is known that the characteristic impedance of a five wire transmission line is as follows:

$$Z = (173/\epsilon_r^{\frac{1}{2}}) \text{Log}_{10}(D/0.933\,d)$$

where
Z = characteristic-impedance of five-wire transmission line
$\epsilon_r$ = relative dielectric constant for test medium
d = diameter of conductors
D = separation between outer conductors Thus the spacing and the wire diameters can be chosen to provide a tip with matching impedance. For example, a test probe incorporated a 50 ohm cable 20 having an outer diameter of 0.141 inch, a shorting disc 50 of the same diameter and wires 0.036 inch diameter "d" having a separation "D" of 0.1 inch. For use with a 10.4 GHz source, the length of the tip should be at least 0.8 inch. For clean oil ($\epsilon_r = 2.2$) the tip with these dimensions has an impedance Z=55.26, according to the above equation. As the oil becomes contaminated the impedance match improves. For oil containing 5% water or soot, $\epsilon_r = 2.5$ and Z=51.84 ohms thus providing a rather good match with a 50 ohm cable.

An advantage of the five wire tip is that the microwave field is contained within the tip and is not radiated outwardly. Consequently, metal objects, that is the engine housing or other portions of the engine near the probe, do not influence the measurements made by the probe.

While it is preferred that the tip have four outer wires, three or five or more may be acceptable as long as the probe meets the requirements of impedance matching, field containment and minimal oil hangup. As the number of wires decreases the field is contained less well, and as the number of wires increases the oil flow becomes more impeded.

Various well-known detection schemes can be used to determine the dielectric constant of the oil which in turn is interpreted as a measure of the degree of contamination of the oil. In any case, the envelope of the standing wave inside the coaxial cable 20 is dependent on the dielectric properties of the oil medium. As the dielectric constant increases this envelope will change. The dielectric constant or the contaminant content can be determined by measuring (1) the voltage level of the standing wave at a fixed position along the coaxial cable 20, (2) the null location of the standing wave along the coaxial cable 20, or (3) the operating frequency of the source required to keep the null or the standing wave at a fixed position along the coaxial cable 20. To implement the option listed first above, as shown in FIG. 1, the diode detector 34 coupled to the coaxial cable will produce an output proportional to the voltage level of the standing wave at that position and the output is displayed by a deflection of the meter 36 which is calibrated to provide the oil contamination information.

In the case of using a microwave probe as a liquid level detector, the same detection arrangement can be utilized. When the oil level drops to a point allowing about 0.1 inch of air or vapor to enter the tip the effective dielectric constant experiences a large change so that a large scale deflection occurs on the meter 36 whereas in the case of oil contamination the meter deflection would be relatively smaller. By locating the line coupler between a null and maximum value of a standing wave (for clean oil) and calibrating the meter 36 accordingly, contamination of the oil will cause meter deflection in one direction (higher voltage) and low oil level will cause meter deflection in the opposite direction. Still another method of detecting dielectric constant changes is the already-known technique of measuring impedance changes using three diode detectors spaced ⅛ wavelength apart along the transmission line as set forth in "Three-Probe Method of Impedance Measurement", W. J. Duffin, *Wireless Engineer*, December 1952, pp. 317–320. Thus a probe and its associated microwave circuit are not limited to separate uses of liquid level detection and contaminant measurement but rather they may both be combined in a single application wherein as long as the probe is fully immersed in the fluid increasing contamination levels are evidenced by one type of signal output and if the oil level decreases below a critical value another type of output will occur.

A specific example of laboratory apparatus used for measuring contaminants in oil with the subject probe by sensing the null location of the standing wave in the transmission line is a line coupler comprising an HP-X810B slotted line serially coupled to an HP-423A detector 34 and an HP-415E SWR meter 36 and energized by an HP-8690B sweep oscillator, all from Hewlett-Packard Corporation of Palo Alto, Calif. and a DBG-480 isolator 30 from Systron Donner, Microwave Division, Van Nuys, Calif.

Although the meter 36 is illustrated as the functional circuit output, other well-known outputs could be used, such as a signal level detector coupled with an indicator to indicate when a predetermined condition has occurred or the measured data may be stored in a memory device for later analysis.

It will thus be seen that as described herein, the microwave probe is an inexpensive, rugged and compact device which may be made very small for access into restricted places and can be configured to have a tip with impedance matching the adjoining coaxial cable to maximize the sensitivity of the probe and to minimize the difficulty in analyzing the signal reflected from the probe.

The embodiments of the invention in which an exclusive property or privilege is claimed are defined as follows:

1. A microwave probe for detecting oil level in the crankcase of an internal combustion engine by measuring the dielectric constant of fluid at a fixed location in the crankcase comprising:
- a coaxial cable having an outer conductive sheath and a concentrically located inner wire;
- a cage-like tip attached to an end of the coaxial cable including a center wire connected to the said inner wire, three to five outer wires each connected at one end to the sheath and surrounding the center wire, the outer wires being spaced sufficiently to facilitate free flow of fluid through the tip and being sufficiently close to contain a microwave field within the tip, and means shorting the distal ends of the said center wire and outer wires the wire geometry and number of wires being so selected that the impedance of the tip, when immersed in the oil, substantially matches the impedance of the coaxial cable, whereby the dielectric constant of the fluid in the tip has one value when the tip is immersed in oil and a substantially different value when the tip is, at most, partially immersed in oil so that a low oil level is readily detected.

2. A microwave probe for detecting oil level in the crankcase of an internal combustion engine by measuring the dielectric constant of fluid at a fixed location in the crankcase comprising;
- a coaxial cable having an outer conductive sheath and a concentrically located inner wire, the inner wire axially extending a fixed distance beyond the sheath,
- a round conductor element having a diameter approximately the same as the sheath diameter connected to the end of the inner wire, and four outer wires parallel to the inner wire connected between the conductor element and the sheath to form a cage-like tip with sufficient space between the wires to allow free fluid flow through the tip, the wire geometry being so selected that the impedance of the tip, when immersed in the liquid, substantially matches the impedance of the coaxial cable, whereby the dielectric constant of the fluid in the tip has one value when the tip is immersed in oil and a substantially different value when the tip is, at most, partially immersed in oil so that a low oil level is readily detected.

3. A microwave probe for detecting oil level in the crankcase of an internal combustion engine by measuring the dielectric constant of fluid at a fixed location in the crankcase comprising;
- a coaxial cable having an outer conductive sheath and a concentrically located inner wire;
- a cage-like tip attached to an end of the coaxial cable consisting of five parallel wires shorted at one end including a center wire connected to the said inner wire, four outer wires each connected at one end to the sheath and surrounding the center wire, the outer wires being spaced sufficiently to facilitate free flow of liquid through the tip, and a shorting conductor connected to the distal ends of the said parallel wires; the wire geometry being so selected that the impedance of the tip, when immersed in the liquid, substantially matches the impedance of the coaxial cable, whereby the dielectric constant of the fluid in the tip has one value when the tip is immersed in oil and a substantially different value when the tip is, at most, partially immersed in oil so that a low oil level is readily detected.

* * * * *